United States Patent [19]

Szilagyi et al.

[11] 4,259,328
[45] Mar. 31, 1981

[54] MORPHOLINO PYRIDAZINYLHYDRAZONES

[75] Inventors: Géza Szilágyi; Endre Kasztreiner; Judit Kosáry; Péter Mátyus; Zsuzsa Huszti; György Cseh; Agnes Kenessey; László Tardos; Edit Kósa; László Jaszlits; Sándor Elek; István Elekes; István Polgári, all of Budapest, Hungary

[73] Assignee: Richter Gedeon Vegyeszeti Gyar Rt, Budapest, Hungary

[21] Appl. No.: 914,778

[22] Filed: Jun. 12, 1978

[30] Foreign Application Priority Data

Jun. 13, 1977 [HU] Hungary ............................ GO 1372

[51] Int. Cl.³ ................. C07D 295/00; A61K 31/535
[52] U.S. Cl. ......................... 424/248.53; 424/248.55; 424/250; 544/114; 544/224; 544/238; 544/239; 544/241
[58] Field of Search ...................... 544/122, 123, 114; 424/248.53, 248.55

[56] References Cited

U.S. PATENT DOCUMENTS 3,535,317 10/1970 Bellasio et al. .................... 260/247.5
3,984,411 10/1976 Claverie et al. ..................... 544/122

OTHER PUBLICATIONS

Shiho et al., "Chem. Abstracts", vol. 50 (1956), p. 4969 (h).
Libermann et al., "Chem. Abstracts", vol. 55 (1961), p. 18737 (b).
Kuraishi, "Chem. Abstracts", vol. 52 (1958), p. 14623 (e).

*Primary Examiner*—Henry R. Jiles
*Assistant Examiner*—R. W. Ramsuer
*Attorney, Agent, or Firm*—Karl F. Ross

[57] ABSTRACT

Pyridazinylhydrazones capable of lowering blood pressure having the formula

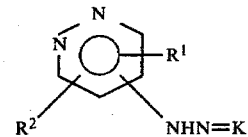

wherein
$R^1$ is hydrogen, chlorine, alkyl having from 1 to 4 carbon atoms, methoxy, hydroxyl, carbamoyl or cyano;
$R^2$ is morpholino; and
K is a group having the formula

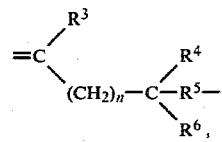

wherein one of $R^3$, $R^4$, $R^5$ or $R^6$ is carboxyl or alkoxycarbonyl.

15 Claims, No Drawings

MORPHOLINO PYRIDAZINYLHYDRAZONES

This invention relates to new pyridazinylhydrazones and pharmaceutically acceptable salts thereof.

More particularly, this invention relates to new pyridazinylhydrazones having the general formula I

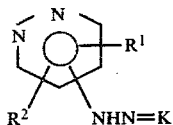

wherein
- $R^1$ is hydrogen, chlorine, alkyl having from 1 to 4 carbon atoms, methoxy, hydroxyl, carbamoyl or cyano;
- $R^2$ is hydrogen, chlorine or $-NR^7R^8$, wherein
  - $R^7$ and $R^8$ each can be hydrogen, alkyl having from 1 to 5 carbon atoms, or hydroxyalkyl having from 2 to 4 carbon atoms, or
  - $R^7$ and $R^8$ together with the nitrogen atom to which they are attached form a morpholine, piperidine, piperazine or N-methylpiperazine ring;
- K is a group having the formula II or a group having the formula III

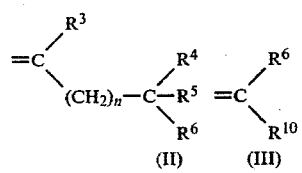

wherein
- $R^3$ is hydrogen, alkyl having from 1 to 10 carbon atoms, cycloalkyl having from 3 to 7 carbon atoms, trifluoromethyl, phenyl, phenyl substituted with chlorine atom, nitro or one or more methoxy groups, pyridyl or alkoxycarbonyl having from 1 to 4 carbon atoms in the alkoxy moiety;
- $R^4$ and $R^5$ each can be hydrogen, alkyl having from 1 to 4 carbon atoms or alkoxycarbonyl having from 1 to 4 carbon atoms in the alkoxy moiety;
- $R^6$ is hydrogen, carboxyl or the group $-CO_2R^9$, wherein $R^9$ is alkyl having from 1 to 9 carbon atoms, hydroxyalkyl having from 2 to 4 carbon atoms, cycloalkyl having from 3 to 7 carbon atoms, $-CONHNH_2$ or $-CONH_2$,
- n is 0, 1, 2, 3, 4 or 5;
- Q is a mono- or bicyclic alkyl having from 3 to 10 carbon atoms; and
- $R^{10}$ is H or an alkyl having from 1 to 6 carbon atoms, with the proviso that when $R^3$ is hydrogen or an alkyl having from 1 to 6 carbon atoms, $R^4$ and $R^6$ both represent hydrogen, and n is 0 then $R^5$ may not represent an alkyl having from 1 to 4 carbon atoms.

Preferred representatives of the compounds having the formula I are those pyridazinylhydrazones, in which
- $R^2$ is chlorine, bis(2-hydroxyethyl)amino, dibenzylamino or morpholino;
- $R^3$ is methyl, phenyl or pyridyl;
- $R^4$ and $R^5$ are hydrogen or methyl;
- $R^6$ is carboxyl, carboxylic acid ester group or carboxamide group;
- Q is a cyclohexane or bornane ring;
- $R^{10}$ stands for methyl and
- n is 0, 1 or 2.

The invention especially relates to compounds of the formula:

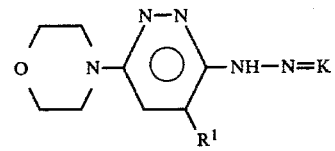

wherein
- $R^1$ is hydrogen, chlorine, alkyl having 1 to 4 carbon atoms, methoxy, hydroxyl, carbamoyl or cyano; and
- K is a group of the formula:

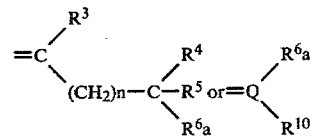

wherein
- $R^3$ is hydrogen, alkyl having 1 to 10 carbon atoms, cycloalkyl having 3 to 7 carbon atoms, or alkoxycarbonyl having 1 to 4 carbon atoms in the alkoxy moiety;
- $R^6$ is a carboxyl or $-CO_2R^9$ wherein $R^9$ is alkyl having 1 to 9 carbon atoms;
- n is 0, 1, 2, 3, 4, or 5;
- Q is a mono- or bicyclic alkyl having 3 to 10 carbon atoms; and $R^{10}$ is alkyl having 1 to 6 carbon atoms, or a pharmaceutically acceptable salt thereof.

Another group of compounds of high interest are compounds of the formula:

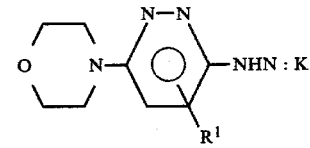

wherein
- $R^1$ is hydrogen, chlorine, alkyl having 1 to 4 carbon atoms, methoxy hydroxy, carbomoyl or cyano; and
- K is a group of the formula:

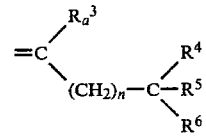

wherein
- $R_a^3$ is alkoxycarbonyl having 1 to 4 carbon atoms in the alkoxy group;
- $R^4$ and $R^5$ are each hydrogen, alkyl having 1 to 4 carbon atoms, or alkoxycarbonyl having 1 to 4 carbon atoms in the alkoxy group;

$R^6$ is hydrogen, carboxyl, or the group $-CO_2R^9$, wherein $R^9$ is alkyl having 1 to 9 carbon atoms; and n is 0, 1, 2, 3, 4, or 5, or a pharmaceutically acceptable salt thereof.

It is well known that in human and higher animal organisms noradrenaline is the most important blood pressure regulating agent (see S. M. Rapoport: Med. Biochemie, VEB Verlag Volk und Gesundheit, Berlin, 720 (1965)). Pathologically high blood pressure can therefore be decreased by inhibition of the biosynthesis of noradrenaline (O. Schier and A. Marxer: Arzneimittelforschung, Vol. 13., Birkhäuser Verlag, Basel, p. 107 (1969)). The first step of this biosynthesis consists in the hydroxylation of tyrosine, wherein thyrosine-hydroxylase enzyme acts as a bio-catalyst, while in the third step dopamine is $\beta$-hydroxylated in the presence of the dopamine-$\beta$-hydroxylase enzyme as a bio-catalyst.

Now it has been surprisingly found that new pyridazinylhydrazone derivatives having the formula I unexpectedly show a considerable tyrosine-hydroxylase and dopamine-$\beta$-hydroxylase inhibiting effect, thereby inhibiting the biosynthesis of noradrenaline and exerting a significant and long-lasting blood pressure lowering activity.

Compounds having the formula I and pharmaceutically acceptable salts thereof are prepared according to the invention by (a) reacting a compound having the formula IV

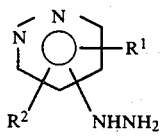

(IV)

wherein $R^1$ and $R^2$ are as defined above with a ketone of the formula V or VI

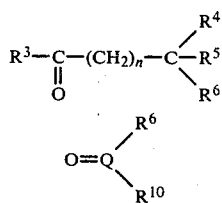

(V)

(VI)

wherein $R^3$, $R^4$, $R^5$, $R^6$, $R^{10}$, Q and n are as defined above, to give compounds of the formula I, in which K stands for a group of the formula II or III, wherein $R^3$, $R^4$, $R^5$, $R^6$, $R^{10}$, Q and n are as defined above; or (b) reacting a compound having the formula IV, wherein $R^1$ and $R^2$ are as defined above, with an acid having the formula VII or VIII

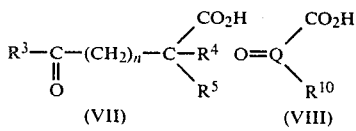

(VII) (VIII)

wherein $R^3$, $R^4$, $R^5$, $R^{10}$, Q and n are as defined above, and treating the thus-obtained acid having the formula IX or X

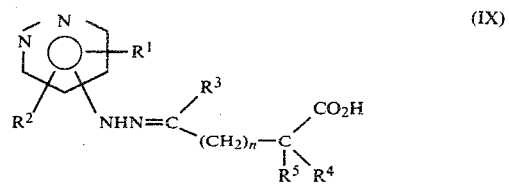

(IX)

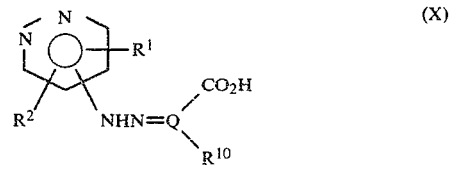

(X)

wherein $R^1$, $R^2$, $R^3$, $R^4$, $R^5$, $R^{10}$, Q and n are as defined above, or a reactive derivative thereof with an alcohol having the formula $R^9OH$, wherein $R^9$ is as defined above—in case of preparing tertiary butyl esters with isobutylene or tertiary-butanol—or with hydrazine or ammonia to prepare compounds of the formula I, wherein K represents the group having the formula II or III wherein $R^3$, $R^4$, $R^5$, $R^{10}$, Q and n are as defined above and $R^6$ is a $CO_2R^9$, $-CONHNH_2$ or $-CONH_2$ group, wherein $R^9$ is as defined above; or (c) reacting a compound of the formula IV, wherein $R^1$ and $R^2$ are as defined above, with an ester having the formula XI

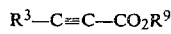
$R^3-C\equiv C-CO_2R^9$ (XI)

wherein $R^3$ and $R^9$ are as defined above, to prepare a compound of the formula I, wherein K represents a group of the formula II, wherein $R^3$ is as defined above, $R^4$ and $R^5$ each are hydrogen, n is 0 and $R^6$ is a group having the formula $-CO_2R^9$, wherein $R^9$ is as defined above, and, if desired, converting a compound of the formula I obtained into an acid addition salt thereof formed with a pharmaceutically acceptable acid.

According to a preferred embodiment of the invention compounds of the formula IV and V or VI are transformed into compounds of the formula I by reacting the two reactants in water or an organic solvent, preferably in an ether, such as diethyl ether or tetrahydrofurane, lower aliphatic alcohols, or aromatic hydrocarbons, such as benzene, toluene, or xylene, at a temperature of 10° C. to 140° C. In some instances it is advantageous to add an acid catalyst, e.g. 4-toluenesulphonic acid or hydrochloric acid, to the reaction mixture.

Out of the starting materials having the formula IV the following compounds have been described in the literature: 3-chloro-6-pyridazinylhydrazine [Yakugaku Zasshi, 75, 778 (1955); C.A. 50, 4970b (1956)];

3,6-dichloro-4-pyridazinylhydrazine [Pharm. Bull., 5, 376 (1957)];

3-pyridazinylhydrazine [Bull. soc. chim. France, 1793 (1959)];

3-methyl-6-pyridazinylhidrazine [J. Pharm. Soc. Jap., 75, 776 (1955)];

3-cyano-6-pyridazinylhydrazine [Hungarian Pat. No. 165,304]; and amino-substituted pyridazinylhydrazines (see for example [J. Med. Chem., 18, 741 (1975)].

Other pyridazinylhydrazines encompassed by the formula IV, which are new according to the state of art are described hereinbelow with presentation of experimental results.

Compounds of the formula V are known in the art. The carboxylic acid esters may be prepared for instance by Grignard reaction of the corresponding cyano compound, or by alkoxycarbonylating the corresponding methyl ketone derivative [see J. Am. Chem. Soc., 63, 2252 (1941) and 67, 2197 (1945)]. Another known method for preparing compounds of the formula V consists in subjecting the corresponding mixed anhydrides to Grignard reaction [Tetrahedron, 33, 595 (1977)].

Acid amides and acid hydrazides can be obtained by reacting the corresponding carboxylic acid esters with suitable amines or hydrazine, respectively [see for example Chem. Ber., 35, 583 (1902); Beilsteins Handbuch der Organischen Chemie, 3, 676].

From compounds of the formula VI cycloalkanone derivatives substituted by an alkoxycarbonyl group in the 2-position are prepared by reacting a corresponding cycloalkanone with an alkyl oxalate in the presence of sodium alcoholate [see e.g. Org. Synth., II, 531].

Cycloalkanone-2-carboxamides are prepared by condensing a corresponding cycloalkanone with urea and subsequently hydrolysing the spiro-compound obtained with an acid [J. Für Prakt. Chemie, 318, 773 (1976)].

Those compounds of the formula VI in which $R^6$ stands for hydrogen are commercially readily available cyclic ketones, such as camphor, carvone or 2-methylcyclohexanone.

Reaction of the compounds having the formula IV with acids having the formula VII or VIII to give acids of the formula IX or X is preferably carried out in the analogy of the preparation of compounds of the formula I when starting from compounds of the formula IV and V.

Starting compounds of the formulae VII and VIII are usually prepared by a mild alkaline hydrolysis of the corresponding carboxylic acid esters [see for instance J. Am. Chem. Soc., 81, 2598 (1959); Liebigs Ann., 699, 33 (1966) and 317, 98 (1901); Chem. Ber., 72, 919 (1939)].

Compounds having the formula IX or X are preferably transformed into compounds having the formula I as described hereinbelow.

When carboxylic acid esters are to be prepared, i.e. in the formula I K stands for a group of the general formula II or III and $R^6$ represents a $CO_2R^9$ group, wherein $R^9$ is as defined above, in the first step compounds of the formula IX or X are transformed into their acid chlorides by means of thionyl chloride. As a solvent an excess amount of thionyl chloride can be used, or the reaction can be conducted in a chlorinated hydrocarbon, such as chloroform or dichloroethane; or in a hydrocarbon, such as benzene. The acid chloride obtained is then reacted with an alcohol having the general formula $R^9OH$ or with an alkali metal alcoholate of same, preferably in an excess amount of the alcohol, at a temperature between 0° C. and the boiling point of the alcohol.

When methyl or ethyl esters are to be prepared, one can proceed also by reacting an acid having the formula IX or X with methanol or ethanol containing gaseous hydrochloric acid.

When the preparation of an acid hydrazine is intended, i.e. in the formula I K represents a group having the general formula II or III and $R^6$ is a $-CONHNH_2$ group, it is advisable to react a methyl or ethyl ester, prepared from a corresponding compound of the formula IX or X as described above, with hydrazine in a methanolic or ethanolic solution.

When an acid amide is to be prepared, i.e. in the formula I K stands for a group having the formula II or III and $R^6$ is a $CONH_2$ group, a methyl or ethyl ester, prepared from a corresponding acid having the formula IX or X as described above, is reacted with ammonia in a methanolic or ethanolic solution.

Esters of the formula XI usually are prepared by reacting suitable alkyl triphenylphosphoranilidene acetates with an acid chloride and subjecting the acylylide obtained to pyrolytic decomposition [Liebigs Annalen, 282 (1977)].

Compounds of the formula I are preferably converted into their acid addition salts by dissolving a base of the formula I for example in ether, methanol, ethanol or isopropanol and adding to the solution obtained a solution of the corresponding inorganic acid in methanol, ethanol or ether or of the suitable organic acid in methanol, ethanol, isopropanol, ether or ketone, dropwise, while cooling. The precipitate is filtered off and recrystallized when necessary.

Preferred representatives of the suitable inorganic acids are: hydrochloric acid, hydrogen bromide, sulphuric acid and phosphoric acid. Tartaric acid, maleic acid, fumaric acid, methanesulphonic acid, ethanesulphonic acid and 4-toluenesulphonic acid are advantageously used as organic acids.

In vitro tyrosine-hydroxylase inhibiting activity (TH inhibiting activity) of the new compounds according to the invention was tested by the method of Nagatsu [Anal. Biochem., 9, 122 (1964)] on rat adrenal homogenate. Radioactive tyrosine was purified by the method elaborated by Ikeda [J. Biol. Chem., 241, 4452 (1966)]. TH activity of the rat adrenal homogenate amounted to $0.64 \pm 8$ nmoles/mg protein/60 min.

Dopamine-$\beta$-hydroxylase inhibiting activity (DBH inhibiting activity) of the compounds according to the invention was tested on bovine adrenal (gland) preparations by a modified version of Nagatsu's method [B.B. Acta, 139 319 (1967)]. Specific activity of the bovine adrenal preparation was found to be $780 \pm 50$ nmoles/mg protein/60 min.

Inhibiting effect of several compounds encompassed by the formula I in comparison with some known compounds is listed in the following Table I.

TABLE I

| Example No. | Concentration of the test compound [mole/liter] | Enzyme inhibiting activity, % | |
|---|---|---|---|
| | | TH | DBH |
| 3 | $10^{-4}$ | 100 | 80 |
| | $10^{-5}$ | 75 | 0 |
| 12 | $10^{-4}$ | 100 | 84 |
| | $10^{-5}$ | 85 | 10 |
| 13 | $10^{-4}$ | 95 | 90 |
| | $10^{-5}$ | 40 | 10 |
| 15 | | 100 | 88 |
| | $10^{-5}$ | 50 | 32 |
| 17 | $10^{-4}$ | 85 | 70 |
| | $10^{-5}$ | 33 | 10 |
| 18 | $10^{-4}$ | 100 | 88 |
| | $10^{-5}$ | 50 | 32 |
| 19 | $10^{-4}$ | 82 | 75 |
| | $10^{-5}$ | 30 | 10 |
| 20 | $10^{-4}$ | 100 | 100 |
| | $10^{-5}$ | 50 | 87 |
| 41 | $10^{-4}$ | 92 | 0 |
| | $10^{-5}$ | 50 | 0 |
| 22 | $10^{-4}$ | 100 | 100 |
| | $10^{-5}$ | 50 | 56 |
| 23 | $10^{-4}$ | — | 70 |

TABLE I-continued

| Example No. | Concentration of the test compound [mole/liter] | Enzyme inhibiting activity, % TH | DBH |
|---|---|---|---|
|  | $10^{-5}$ | — | 50 |
| 24 | $10^{-4}$ | — | 100 |
|  | $10^{-5}$ | — | 50 |
| 28 | $10^{-4}$ | 0 | 90 |
|  | $10^{-5}$ | 0 | 71 |
| 29 | $10^{-4}$ | 50 | 70 |
|  | $10^{-5}$ | 0 | 47 |
| 30 | $10^{-4}$ | 50 | 70 |
|  | $10^{-5}$ | 0 | 22 |
| 34 | $10^{-4}$ | — | 100 |
|  | $10^{-5}$ | — | 40 |
| 37 | $10^{-4}$ | — | 100 |
|  | $10^{-5}$ | — | 41 |
| 49 | $10^{-4}$ | — | 66 |
|  | $10^{-5}$ | — | 50 |
| 50 | $10^{-4}$ | — | 73 |
|  | $10^{-5}$ | — | 0 |
| 52 | $10^{-4}$ | 65 | 30 |
|  | $10^{-5}$ | 40 | 0 |
| 55 | $10^{-4}$ | — | 50 |
|  | $10^{-5}$ | — | 0 |
| 62 | $10^{-4}$ | — | 60 |
|  | $10^{-5}$ | — | — |
| 64 | $10^{-4}$ | 36 | 50 |
|  | $10^{-5}$ | 10 | 0 |
| 65 | $10^{-4}$ | — | 73 |
|  | $10^{-5}$ | — | 44 |
| Fusaric acid | $10^{-4}$ | 0 | 100 |
|  | $10^{-5}$ | 0 | 100 |
| D,L-α-methyl-4-hydroxy-phenyl-alanine | $10^{-4}$ | 100 | 0 |
|  | $10^{-5}$ | 60 | 0 |

Blood pressure lowering activity of the new compounds according to the invention was tested on spontaneous hypertensive rats (Wistar-Okamoto rats) following the method described in Arzn. Forsch., 6, 222 (1956). Systolic blood pressure of waking animals was measured in arteria caudalis 4, 24, 48 and 72 hours after the oral administration of the test compounds. The results obtained are set forth in the following Table II.

TABLE II

| Example No. | Reduction in blood pressure, % 50 mg/kg dose 4 hours | 24 hours | Acute toxicity [LD$_{50}$] on mice mg/kg p.o. |
|---|---|---|---|
| 10 | −41* | −26* | <200 |
| 17 | −23 | −13 | 300 |
| 19 | −8 | −9 | >200 |
| 20 | −25 | −25 | 530 |
| 23 | −21 | −8 | 200 |
| 25 | −33 | −17 | 200 |
| 26 | −38 | −29 | 200 |
| 28 | −29 | −25 | >200 |
| 29 | −30 | −15 | 250 |
| 30 | −31 | −14 | 250 |
| 38 | −34 | −27 | 200 |
| 43 | −32 | −18 | 200 |
| 48 | −33* | −8* | 200 |
| 49 | −22+ | −13+ | <200 |
| 50 | −28+ | −30+ | 200 |
| 52 | −21× | −9× | 400 |
| 53 | −32 | −27 | 200 |
| 55 | −39+ | −14+ | >200 |
| 56 | −20+ | 0+ | >200 |
| 57 | −28* | −16* | 200 |
| 62 | −29 | −26 | 200 |
| 64 | −25 | −11 | >200 |
| 65 | −18 | −23 | >200 |
| Fumaric acid | −33 | 0 | 80 (i.p.) |

TABLE II-continued

| Example No. | Reduction in blood pressure, % 50 mg/kg dose 4 hours | 24 hours | Acute toxicity [LD$_{50}$] on mice mg/kg p.o. |
|---|---|---|---|
| acid |  |  |  |

× = 1.25 mg/kg
* = 2.5 mg/kg
+ = 20 mg/kg.

Out of the compounds tested the compounds prepared in Examples 10, 17, 20, 23, 25, 26, 27, 28, 29, 30, 38, 43, 48, 49, 50, 52, 53, 55, 56, 57, 62, 64 and 65 showed a significant blood pressure lowering activity ($\geq -15\%$). Effect of the compounds 29 and 30 lasted 72 hours when they were used in a dose of 50 mg/kg. This period lasted 48 hours when the dose employed was 20 mg/kg. Acute oral toxicity and consequently therapeutic index of these compounds tested on rats are also favorable.

Biochemical and pharmacological experiments show that a lasting and strong blood pressure lowering effect appears together with the strong enzyme inhibiting effect. Compounds of the formula I can be used in the therapy in a daily dose of 50 to 3000 mg.

Further details of the invention are given in the following non-limiting Examples.

EXAMPLE 1

1,7,7-Trimethyl-2-bicyclo[2,2,1]heptylidene-(3-chloro-6-pyridazinyl)-hydrazone

Method (a)

A mixture of 30.4 g. (0.2 moles) of camphor, 29 g. (0.2 moles) of 3-chloro-6-pyridazinylhydrazine, 500 ml. of ethanol and 50 ml. of glacial acetic acid is kept at boiling temperature for three hours. The solvent is then distilled off in vacuo, the evaporation residue admixed with 200 ml. of water and adjusted to neutral under cooling with a 10% sodium carbonate solution. The precipitate obtained is filtered off, washed to neutral with water and dried. Recrystallization from ethanol affords 37.8 g. (67.5%) of the named compound, melting at 103° C. to 105° C.

The hydrochloric acid salt of the product obtained is prepared by suspending the base in ether and saturating the suspension with gaseous dry hydrochloric acid. The precipitate formed is filtered off, washed with ether and dried. M.p. of the acid addition salt obtained: 178° C. (decomposition).

Method (b)

A mixture of 3.04 g. (20 mmoles) of camphor, 2.9 g. (20 mmoles) of 3-chloro-6-pyridazinylhydrazine, 50 ml. of ethanol and 2 drops of a concentrated hydrochloric acid solution is boiled for one and a half hours. Thereafter following the procedure described in Method (a) 3.2 g. (57%) of the named compound melting at 102° C. to 105° C. are obtained.

Method (c)

In a flask equipped with a Dean-Stark water separator a mixture of 3.04 g. (20 mmoles) of camphor, 2.9 g. (20 mmoles) of 3-chloro-6-pyridazinylhydrazine, 70 ml. of benzene and 0.1 g. of 4-toluenesulphonic acid is boiled until the calculated amount of water is separated. Thereafter proceeding as described in Method (a) 3.3 g. (58.5%) of the named compound melting at 103° C. to 105° C. are obtained.

Compounds of the formula I and acid addition salts thereof which may be prepared by the above procedure are listed in the following Table III.

TABLE III

| Example No. | Compound | Melting point (°C.) | Yield* (%) |
|---|---|---|---|
| 2 | 2,2-Dimethyl-3-bicyclo-[2,2,1]heptylidine | 168 (b)** | 78.5 |
| 3 | 1,7,7-Trimethy-2-bicyclo-[2,2,1]heptylidene-B | 133 to 135 | 60 |
| 4 | 1-(2,6,6-Trimethyl-1-,cyclohexenyl-1-ethylidene-A | 180 to 182 | 58.5 |
| 5 | 1-Methyl-4-isopropenyl-2-cyclohex-6-enylidene-A | 137 to 138 | 57 |
| 6 | 1,7,7-Trimethyl-2-bicyclo-[2,2,1]heptylidiene-[3-(4-methyl-1-piperazinyl)-6-pyridazinyl]hydrazine | 201 to 204 | 40.5 |
| 7 | 1-(2-Bicyclo[2,2,1]hept-5-enyl)-1-ethylidene-A | 91 to 93 | 30.5 |
| 8 | 1-Methyl-4-isopropyl-3-cyclohexylidene-A | 130 to 132 | 38.5 |
| 9 | 1-Methyl-4-isopropylidene-3-cyclohexylidene-A | 132 to 135 | 32 |
| 10 | Cyclohexylidene-D | 159 to 161 | 42.5 |
| 11 | 2-(Ethoxy-carbonyl)-1-cyclohexylidene-D | 58 to 60** | 79 |
| 12 | Cyclohexylidene-B | 134 to 136 | 17 |
| 13 | 1-Phenyl-1-ethylidene-B | 153 to 155 | 44.5 |
| 14 | Cyclohexylidene-C | 104 to 105 | 58 |
| 15 | 2-Methyl-1-cyclohexylidene-A | 115 to 118 | 63 |
| 16 | 2,6-Dimethyl-1-cyclohexylidene-A | 92 to 93 | 58.5 |
| 17 | 2-(Ethoxycarbonyl)-1-cyclohexylidene-A | 115 to 117 | 55.5 |
| 18 | 2-Carboxy-1-cyclohexylidene-A | 238 to 241 | 22.5 |
| 19 | 2-carboxy-1-cyclohexylidene-B | 208 to 200 | 18.5 |

Remarks:
A = 3-chloro-6-pyridazinylhydrazone
B = 3-pyridazinylhydrazone
C = 3,6-dichloro-4-pyridazinylhydrazone
D = 3-morpholino-6-pyridazinylhydrazone
* = yield values after recrystallization
** = HCl salt
(b) = decomposition compounds 10, 12, and 14 are products in which Q is cyclohexane and $R^{10}$ and $R^6$ are H.

EXAMPLE 20

3-(Ethoxycarbonyl)-2-propylidene-(3-chloro-6-pyridazinyl)hydrazone

Method (a)

A mixture of 4.35 g. (30 moles) of 3-chloro-6-pyridazinylhydrazine, 3.93 g. (30 mmoles) of ethyl acetacetate and 36 ml. of ethanol is stirred at room temperature for 8 hours and then allowed to stand overnight. Thereafter ethanol is evaporated in vacuo, the residue is triturated with ether, filtered and dried. 5.6 g. (72.5%) of the named compound are obtained, melting at 124° C. to 127° C.

The corresponding hydrochloric acid salt is prepared as described in Example 1, Method (a). Melting point: 143° to 145° C.

The compounds having the formula I listed in the following Table IV are prepared by the procedure described above.

TABLE IV

| Example No. | Compound | Melting point (°C.) | Yield* % |
|---|---|---|---|
| 21 | 1-(Methoxycarbonyl)-1-ethylidene-A | 203 to 205 | 41 |
| 22 | 3-(Ethoxycarbonyl)-2-propylidene-(3-pyridazinyl) hydrazone | 170 to 173 | 28.5 |
| 23 | 4-Methoxycarbonyl)2-butylidene-A | 121 to 123 | 62.5 |
| 24 | 3-(Methoxycarbonyl)-2-propylidene-A | 124 to 125 | 70 |
| 25 | 3-(Ethoxycarbonyl)-2-butylidene-A | 79 to 81 | 49 |
| 26 | 5-(Ethoxycarbonyl-2-pentylidene-A | 55 to 56 | 69.5 |
| 27 | 1-(Ethoxycarbonyl)-2-butylidene-A | 107 to 108 | 32.5 |
| 28 | 3-(Propoxycarbonyl)-2-propylidene-A | 101 to 103 | 67.5 |
| 29 | 3-(Isopropoxycarbonyl)-2-propylidene-A | 128 to 129 | 59.5 |
| 30 | 3-(tert.-Butoxycarbonyl)-2-propylidene-A | 136 to 137 | 66 |
| 31 | 3-(Octyloxycarbonyl)-2-propylidene-A | 69 to 72 | 57 |
| 32 | 3-(Cyclohexyloxycarbonyl)-2-propylidene-A | 106 to 108 | 70 |
| 33 | 1-(Ethoxycarbonyl)-3,3,3-trifluoro-2-propylidene-A | 158 to 160 | 64.5 |
| 34 | 1-(Ethoxycarbonyl)-2-phenyl-2-ethylidene-A | 131 to 132 | 66 |
| 35 | 1-Ethoxycarbonyl)-2-(4-nitrophenyl)-2-ethylidene-A | 183 to 185 | 74.5 |
| 36 | 1-(Ethoxycarbonyl)-2-(3,4,5-trimethoxyphenyl)-2-ethylidene-A | 139 to 141 | 47.5 |
| 37 | 1-(Ethoxycarbonyl)-2-(3-pyridyl)-2-ethylidene-A | 145 to 146 | 60 |
| 38 | 4-Carboxy-2-butylidene-A | 194 to 196 | 68 |
| 39 | 6-Carboxy-2-hexylidene-A | 184 to 187 | 67 |
| 40 | 1-(Ethoxycarbonyl)-1-ethylidene-B | 175 to 176 | 50 |
| 41 | 3-(Ethoxycarbonyl)-2-propylidene-(3,6-dichloro-4-Pyridazinyl) hydrazone | 82 to 83 | 60.5 |
| 42 | 3-(Ethoxycarbonyl)-2-propylidene-(3-chloro-5-ethylamino-6-pyridazinyl) hydrazone | 88 to 90 | 40 |
| 43 | 4-(tert.-Butoxycarbonyl)-2-butylidene-A | 96 to 99 | 73.5 |
| 44 | (Ethoxycarbonyl)-methylidene-A | 224 to 226 | 79 |
| 46 | 4-(Methoxycarbonyl)-2-butylidene-B | 124 to 127 | 34 |
| 47 | 4-(tert.-Butoxycarbonyl)-2-butylidene-B | 107 to 110 | 43 |
| 48 | 4-Carboxy-2-butylidene-B | 192 to 193 | 59.5 |
| 49 | 6-(Ethoxycarbonyl)-2-hexylidene-A | 33 to 35 | 33 |
| 50 | 5-Carboxy-2-pentylidene-A | 170 to 173 | 68 |
| 51 | 3-(Isopropoxycarbonyl)-2-propylidene-B | 120 to 122 | 35.5 |
| 52 | 3-(tert.-Butoxycarbonyl)-2-propylidene-B | 143 to 145<br>187 to 189** | 73 |
| 53 | 3-(tert.-Butoxycarbonyl)-2-propylidene-(3-methyl-6-pyridazinyl) hydrazone | 98 to 99 | 38 |
| 54 | 3-(Ethoxycarbonyl)-2-propylidene-(3-hydroxy-6-pyridazinyl) hydrazone | 175 to 178 | 31 |
| 55 | 4-Carboxy-2-butylidene-(3-methyl-6-pyridazinyl) hydrazone | 164 to 167 | 42 |
| 56 | 3-(tert.-Butoxycarbonyl)-2-propylidene-(3-carbamoyl-6-pyridazinyl) hydrazine | 204 to 207 | 92 |
| 57 | 5-Carboxy-2-pentylidene-B | 183 to 186 | 34.5 |
| 58 | 5-(tert.-Butoxycarbonyl)-2-pentylidene-B | oil | 29 |
| 59 | 3-(tert.-Butoxycarbonyl) | | |

TABLE IV-continued

| Example No. | Compound | Melting point (°C.) | Yield* % |
|---|---|---|---|
| | 2-propylidene-(3-cyano-6-pyridazinyl) hydrazine | | |
| 60 | 3-(tert.-Butoxycarbonyl)-2-propylidene-[3-bis(hydroxy-ethylamino)-6-pyridazinyl]-hydrazine | oil | 37.5 |
| 61 | 3-(tert.-Butoxycarbonyl)-2-propylidene-[3-(2-hydroxy-propyl-methylamino)-6-pyridaziny] hydrazine | oil | 36 |

Remarks:
A = 3-chloro-6-pyridazinyhydrazone
B = 3-morpholino-6-pyridazinylhydrazone
* = yield values after recrystallization
** = HCl salt Method (b)

A mixture of 0.72 g. (5 mmoles) of 3-chloro-6-pyridazinylhydrazine, 100 ml. of an aqueous solution containing 1.02 g. (5 mmoles) of potassium hydrogenphthalate and 0.65 g. (5 mmoles) of ethyl acetacetate is stirred at room temperature for 40 minutes. The precipitate formed is filtered off, washed with water and dried. 1.0 g. (77.5%) of the named compound is obtained.

EXAMPLE 62

4-(Ethoxycarbonyl)-2-butylidene-(3-chloro-6-pyridazinl)hydrazone

A mixture of 1.21 g. (5 mmoles) of 4-carboxy-2-butylidene-(3-chloro-6-pyridazinyl)hydrazine and 10 ml. of a 10% aqueous hydrochloric acid solution is stirred at room temperature for 5 hours. The reaction mixture is poured into 25 ml. of water, its pH-value is adjusted to neutral with ammonia and the precipitate formed is filtered off, washed with water and recrystallized from ethanol. 0.8 g. (59%) of the named compound are obtained, melting at 98° C. to 99° C.

EXAMPLE 63

1-(Ethoxycarbonyl)-1-ethylidene-(3-chloro-6-pyridazinyl)hydrazone

Method (a)

Following the procedure described in Example 20, method (a) but starting from 1.45 g. (10 mmoles) of 3-chloro-6-pyridazinylhydrazine and 1.16 g. (10 mmoles) of ethyl pyruvate, 1.17 g. (52%) of the named compound melting at 174° to 177° C. are obtained.

Method (b)

A mixture of 2.15 g. (10 mmoles) of 1-carboxy-1-ethylidene-(3-chloro-6-pyridazinyl)hydrazone, 1.19 g. (11 mmoles) of ethyl bromide, 1.1 g. (11 mmoles) of triethylamine and 20 ml. of ethanol is boiled for 10 hours with stirring. The reaction mixture is allowed to cool to room temperature and the precipitate formed is filtered off, the filtrate is evaporated in vacuo and the residue is triturated with 6 ml. of water. The precipitated crystals are filtered off, washed with water and recrystallized from ethanol to give 0.85 g. (35% of) the named compound.

EXAMPLE 64

1,2-di-(methoxycarbonyl)-ethylidene-(3-chloro-6-pyridazinyl)hydrazone

To a stirred mixture of 14.45 g. (0.1 moles) of 3-chloro-6-pyridazinylhydrazine and 100 ml. of dioxane a mixture of 14.21 g. (0.1 moles) of dimethyl acetylenedicarboxylate and 75 ml. of dioxane is added dropwise at room temperature in 30 minutes. The reaction mixture is stirred for further 5 hours. The dioxane is then evaporated in vacuo and the residue recrystallized from ethanol to afford 19.5 g. (68.5%) of the named compound, melting at 138° C. to 141° C.

3-(Ethoxycarbonyl)-2-propylidene-(3-chloro-6-pyridazinyl)hydrazone (Example 20) was prepared by the same procedure, yield: 38.5%.

EXAMPLE 65

2-(Ethoxycarbonyl)-1-ethylidene-(3-chloro-6-pyridazinyl)hydrazone

One proceeds as described in Example 64, with the difference that ethyl propiolate is used as starting material; yield: 65%; m.p. 115° C. to 117° C.

EXAMPLE 66

2-(Ethoxycarbonyl)-1-ethylidene-(3-morpholino-6-pyridazinyl)hydrazone

One proceeds as described in Example 64, with the difference that ethyl propiolate and the corresponding 3-morpholino-6-pyridazinyl hydrazine are used as starting materials; yield 43%; m.p. 180° C. to 184° C.

EXAMPLE 67

3-Carbamoyl-2-propylidene-(3-chloro-6-pyridazinyl)-hydrazone

A mixture of 0.725 g. (5 mmoles) of 3-chloro-6-pyridazinylhydrazine, 0.5 g. (5 mmoles) of acetacetamide and 40 ml. of tetrahydrofurane is stirred at room temperature for 6 hours and subsequently allowed to stand overnight. The precipitate formed is filtered off, washed with tetrahydrofurane and dried. 0.48 g. (42%) of the named compound melting at 178° C. to 180° C. are obtained.

EXAMPLE 68

Oral tablets, containing 200 mg. of active ingredient and having the following composition are prepared:

| | | |
|---|---|---|
| 3-(tert.-butoxycarbonyl)-2-propylidene-(3-morpholino-6-pyridazinyl) hydrazone | 200 | mg. |
| microcrystalline cellulose | 146.4 | mg. |
| colloidal silica | 1.8 | mg. |
| magnesium stearate | 1.8 | mg. |
| The tablets are covered by a film coat. Average weight: 350 mg. | | |

Injection preparate:

Ampoules for parenteral application contain 25 mg. of active ingredient (expressed in base). The active ingredient is present in a sterile, frozen-dried form.

We we claim is:

1. A compound of the formula:

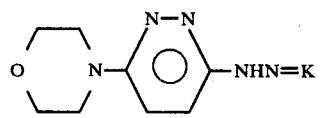

wherein
K is a group of the formula:

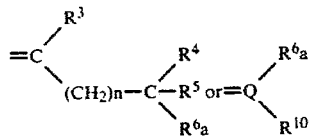

wherein
- $R^3$ is hydrogen, alkyl having 1 to 10 carbon atoms, cycloalkyl having 3 to 7 carbon atoms, or alkoxycarbonyl having 1 to 4 carbon atoms in the alkoxy moiety;
- $R^4$ and $R^5$ are each hydrogen, alkyl having 1 to 4 carbon atoms, or alkoxycarbonyl having 1 to 4 carbon atoms in the alkoxy moiety;
- $R_a^6$ is a carboxyl or $-CO_2R^9$ wherein $R^9$ is alkyl having 1 to 9 carbon atoms;
- n is 0, 1, 2, 3, 4 or 5
- Q is a mono- or bicyclic alkyl having 3 to 10 carbon atoms; and
- $R^{10}$ is alkyl having 1 to 6 carbon atoms, or a pharmaceutically acceptable salt thereof.

2. A 3-($C_1$ to $C_9$ alkoxycarbonyl)-2-propylidene-(3-morpholino-6-pyridazinyl)-hydrazone as defined in claim 1 or a pharmaceutically acceptable salt thereof.

3. A 3-ethoxy, 3-isopropoxy, or 3-tert.-butoxy-carbonyl-2-propylidene-(3-morpholino-6-pyridazinyl)-hydrazone or a pharmaceutically acceptable salt thereof.

4. The compound defined in claim 1 selected from the group consisting of:
- 4-(t-butoxycarbonyl)-2-butylidene-(3-morpholino-6-pyridazinyl)-hydrazone;
- 4-carboxy-2-butylidene-(3-morpholino-6-pyridazinyl)-hydrazone;
- 3-isopropoxycarbonyl-2-propylidene-(3-morpholino-6-pyridazinyl)-hydrazone;
- 3-t-butoxycarbonyl-2-propylidene-(3-morpholino-6-pyridazinyl)-hydrazone;
- 5-carboxy-2-pentylidene-(3-morpholino-6-pyridazinyl)-hydrazone; and
- 2-(ethoxycarbonyl)-1-ethylidene-(3-morpholino-6-pyridazinyl)-hydrazone, or a pharmaceutically acceptable salt thereof.

5. The compound defined in claim 1 which is 3-(tert-butoxycarbonyl)-2-propylidene-(3-morpholino-6-pyridazinyl)-hydrazone or a pharmaceutically acceptable salt thereof.

6. A compound defined in claim 1 which is 2-(ethoxycarbonyl)-1-cyclohexylidene-(3-morpholino-6-pyridazinyl)-hydrazone, or a pharmaceutically acceptable salt thereof.

7. The compound defined in claim 1 which is 4-(tert-butoxycarbonyl)-2-butylidene-(3-morpholino-6-pyridazinyl)-hydrazone, or a pharmaceutically acceptable salt thereof.

8. The compound defined in claim 1 which is 4-carboxy-2-butylidene-(3-morpholino-6-pyridazinyl)-hydrazone or a pharmaceutically acceptable salt thereof.

9. The compound defined in claim 1 which is 3-(isopropoxycarbonyl)-2-propylidene-(3-morpholino-6-pyridazinyl)-hydrazone or a pharmaceutically acceptable salt thereof.

10. A pharmaceutical composition having a blood pressure lowering property, which comprises a pharmaceutically effective amount of 50 to 3,000 mgs per day of a compound defined in claim 1 or a pharmaceutically acceptable salt thereof.

11. A method of lowering blood pressure in an animal subject having an elevated blood pressure, which comprises administering to said subject an effective dose of a compound as defined in claim 1 or a pharmaceutically acceptable salt thereof.

12. A compound of the formula:

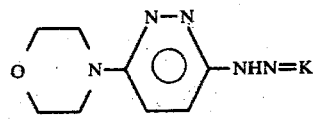

wherein
K is a group of the formula

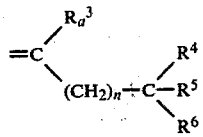

wherein
- $R_a^3$ is alkoxycarbonyl having 1 to 4 carbon atoms in the alkoxy group;
- $R^4$ and $R^5$ are each hydrogen, alkyl having 1 to 4 carbon atoms, or alkoxycarbonyl having 1 to 4 carbon atoms in the alkoxy group;
- $R^6$ is hydrogen, carboxyl, or the group $-CO_2R^9$, wherein
- $R^9$ is alkyl having 1 to 9 carbon atoms; and
- n is 0, 1, 2, 3, 4, or 5 or a pharmaceutically acceptable salt thereof.

13. The compound defined in claim 12 which is 1-ethoxycarbonyl-1-ethylidene-(3-morpholino-6-pyridazinyl)-hydrazone, or a pharmaceutically acceptable salt thereof.

14. A pharmaceutical composition having a blood pressure lowering property, which comprises a pharmaceutically effective amount of 50 to 3,000 mg/day of a compound defined in claim 12 or a pharmaceutically acceptable salt thereof.

15. A method of lowering blood pressure in an animal subject having an elevated blood pressure, which comprises administering to said subject an effective dose of a compound defined in claim 12, or a pharmaceutically acceptable salt thereof.

* * * * *